United States Patent [19]

Li et al.

[11] Patent Number: 5,622,172

[45] Date of Patent: Apr. 22, 1997

[54] ACOUSTIC DISPLAY SYSTEM AND METHOD FOR ULTRASONIC IMAGING

[75] Inventors: Ming Li, Seattle; Jin Kim, Issaquah, both of Wash.

[73] Assignee: Siemens Medical Systems, Inc., Iselin, N.J.

[21] Appl. No.: 536,509

[22] Filed: Sep. 29, 1995

[51] Int. Cl.$^6$ ........................................ A61B 8/00
[52] U.S. Cl. ........................................ 128/661.1
[58] Field of Search .................. 128/660.04, 660.05, 128/660.06, 660.07, 660.08, 660.09, 661.09, 661.1, 916

[56] References Cited

U.S. PATENT DOCUMENTS

| | | | |
|---|---|---|---|
| 4,805,622 | 2/1989 | Riedlinger et al. | 128/660.06 |
| 5,150,714 | 9/1992 | Green | 128/660.06 |
| 5,329,929 | 7/1994 | Sato et al. | 128/661.09 |
| 5,488,952 | 2/1996 | Schoolman | 128/660.07 |

OTHER PUBLICATIONS

"Three-dimensional virtual acoustic displays," by Elizabeth M. Wenzel of NASA Ames Research Center, date unknown, chapter 15 of unknown book, including reference list from same book.

Primary Examiner—George Manuel
Attorney, Agent, or Firm—Jeffrey Slusher

[57] ABSTRACT

An ultrasonic imaging system has a three-dimensional acoustic display. Beam-formed ultrasound scan signals are separated into channel signals and are then filtered using head-related transfer function (HRTF) filters. An HRTF is associated with each of several points in an interrogation region. A filter coefficient processor selects, for each channel signal, a set of HRTF filter parameters according to which sample volume the channel signal comes from. Each HRTF parameter set defines left-ear and right-ear response functions to a calibration sound generated at a calibration point in a calibration space; the calibration point itself corresponds to a predetermined position in the interrogation region. The HRTF-filtered channel signals are then combined into left and right audio output signals which drive left and right speakers that the user listens to while performing the ultrasound scan. The calibration points in the calibration space are mapped to respective reference sample volumes located in a predetermined ultrasonic interrogation region.

5 Claims, 3 Drawing Sheets

ACOUSTIC DISPLAY SYSTEM AND METHOD FOR ULTRASONIC IMAGING

BACKGROUND OF THE INVENTION

1. Field of the Invention

This invention involves a system and a method for presenting ultrasonic scan data acoustically to a user.

2. Description of the Related Art

Various imaging systems such as magnetic resonance imaging (MRI), CT scans, and medical ultrasound have greatly improved the ability to sense the internal structures of human bodies. These imaging systems have provided valuable diagnostic information for various diseases and pathologies and to date the preferred way of presenting information derived from imaging has been visual. In medical ultrasound, however, the Doppler wave form has been presented as a stream of stereo sound through a pair of left-right speakers; such an acoustic display has played an important part in the diagnostic process.

With the rapid progress in computational circuitry, modem ultrasound scanners have become ever more complex and powerful and have been able to acquire and process much more data from each scan. As computational power increases, so too does the need for more effective ways of presenting the ever-richer information available to the sonographer. The most effective way to present complex information to a human is to engage more than one sense: for example, hearing and touch as well as sight. Next to sight, sound information is the easiest to control and present and is best for effectively conveying information.

Psychoacoustic and psychological studies have indicated that audio information is particularly well suited for monitoring state changes over time and that hearing is a primarily time-dependent sense—one can easily hear a gradual change of tone in music but cannot as easily discern a gradual change in brightness of light. Audio signals are, moreover, detected more quickly than visual signals and they tend to cause more alerting and orienting responses. This feature of human physiology quickly brings a new sound event to our attention and also allows us to "filter out" sustained or uninteresting sounds and relegate them to the background. This is known as the "cocktail party effect": one can normally concentrate on and hear a juicy conversation even over the drone of a fan and the voice of a chatty, boring fellow guest.

One's keen sense of hearing and ability to discriminate sounds is especially useful in improving the intelligibility of noise sources and in segregating multiple sound sources. Various acoustic features such as temporal onsets and stops, timbre, pitch, intensity and rhythm can specify the identity of sound objects and convey meaning about discrete events or ongoing actions. Even the simple left-right stereo presentation of ultrasonic scan data has proven to be very helpful in indicating changes in, for example, cardiac blood flow, to the sonographer.

One other advantage of presenting information in the form of sound is that one does not need to be looking at a display screen in order to receive useful information. This is especially helpful during an ultrasonic scan of a patient, since the operator must otherwise look away frequently from the area where she is holding the transducer to see what is being presented visually on the screen.

One drawback of existing acoustic displays of ultrasound scan data is that they are purely "linear," with the apparent source always lying on a line between the user's ears. This is a gross simplification, since the flow velocity vectors one is attempting to "hear" usually have components in at least two dimensions, not just one. Like listening over stereo headphones to the recorded music of a large orchestra, one gets no feeling of depth, only of left and right.

What is needed is therefore a system for displaying ultrasonic scan data acoustically in such a way that a sonographer's ability to localize sound sources in more than one dimension is put to use, so that more of the information obtained from the ultrasound scan is discernible. The system should also allow the user to use both sight and hearing to receive and interpret the scan data.

SUMMARY OF THE INVENTION

The invention provides an ultrasonic imaging system with a three-dimensional acoustic display.

In the preferred embodiment, this is accomplished by scanning an interrogation volume of a patient's body with a transducer at a plurality of scanned sample volumes. A beamformer then forms a beam of returned signals from each respective scanned sample volume for each of a predetermined number of independent velocity directions. Channel separation and projection circuits then convert each beam into a plurality of channel signals; alternatively, the channel separation and projection circuits can operate on previous scan data stored in a conventional cine memory.

A filter coefficient processor then selects, for each channel signal, one of a plurality of predetermined head-related transfer function (HRTF) parameter sets according to a predetermined function of the position in the interrogation region of the corresponding scanned sample volume and of the respective independent velocity direction. Each HRTF parameter set defines left-ear and right-ear response functions to a calibration sound generated at a calibration point in a calibration space; the calibration point itself corresponds to a predetermined position in the interrogation volume. An HRTF filter then filters each channel signal as a predetermined function of the corresponding HRTF parameter set. The HRTF-filtered channel signals are then combined into left and right audio output signals.

A speaker system combines the audio output signals into audio display signals, which are used to drive first and second speakers. The user thereby hears the combined audio display signals as if they were coming from non-colinear points of origin.

In a calibration mode, a pair of head-related transfer functions (HRTF) is determined for each of a plurality of calibration points in a predetermined calibration space. The HRTF's in each pair correspond to left-ear and right-ear response functions to a calibration sound generated at the respective calibration points. One then maps the position of the calibration points in the calibration space to respective reference sample volumes located in a predetermined ultrasonic interrogation region.

DETAILED DESCRIPTION

Figure 1:
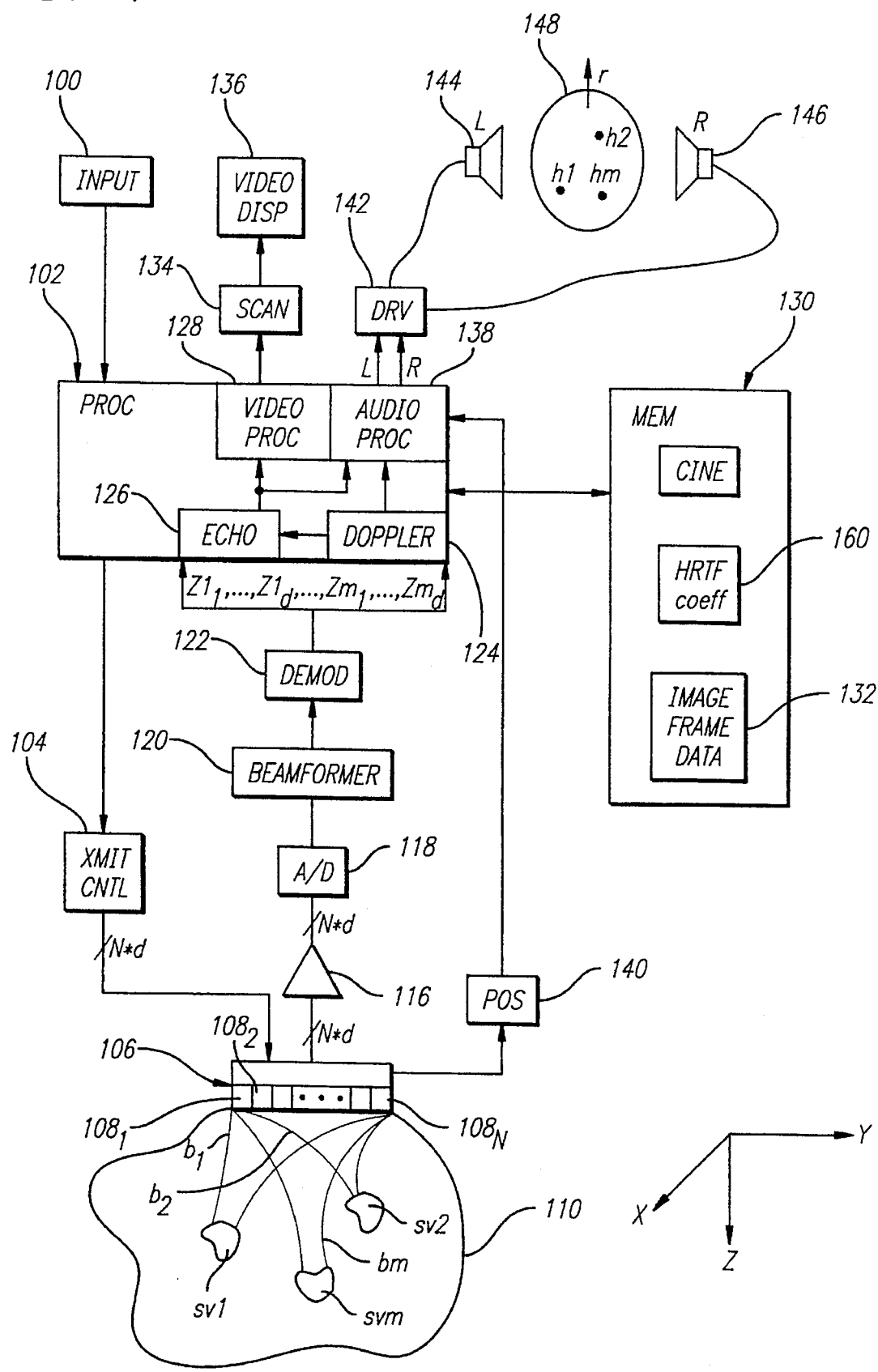
FIG. 1 is a block diagram of a preferred embodiment of a system according to the invention for generating a 3-D acoustic display of ultrasound scan data.

FIG. 1 illustrates the main components of an ultrasonic imaging system according to the invention. The user enters the various conventional scan parameters into an input unit 100, which typically includes such devices as a keyboard 101, knobs, and buttons. The input unit is connected to a processing system 102, which will typically be an electrically connected and cooperating group of processors such as microprocessors and digital signal processors; the processing system may, however, also be implemented by a single processor as long as it is fast enough to handle the various tasks described below.

As in known systems, the processing system 102 sets, adjusts, and monitors the operating parameters of a conventional transmission control circuit 104, which generates and applies electrical control and driving signals to an ultrasonic probe 106, which includes an array of N piezoelectric elements $108_1, 108_2, \ldots, 108_N$. As is well known in the art, the piezoelectric elements generate ultrasonic waves when electrical signals of the proper frequency are applied to them.

By placing the probe 106 against the body of a patient, these ultrasonic waves enter a portion 110 (an interrogation region) of the patient's body. By varying the phasing, amplitude, and timing of the driving signals in a conventional manner, the ultrasonic waves are focussed to form a series of scan lines that typically fan out from the probe. Using conventional focussing and interleaving techniques, the piezoelectric elements are activated such that the scan lines are formed into m scan beams, three of which are shown in the figure as b1, b2, bm. Each scan beam normally will include a scan line or signal from each of the N elements in the array; the separate scan lines have been omitted from FIG. 1 for the sake of clarity. Each beam is focussed in a known manner on a respective sample volume sv1, sv2, svm.

In the most common applications of ultrasonic scanning, with linear arrays, 2-D images are created and all of the sample volumes sv1, sv2, . . . , svm are small and lie approximately in the same scan plane. In other words, the interrogation region 110 is scanned as a pattern of 2-D planes in order to generate 2-D images. Other techniques using 2-D ultrasound arrays are, however, known that allow the scan beams b1, b2 . . . bm to lie in different planes and thus to generate 3-D representations of the scanned region, and to sense flow with three independent velocity components. The invention is able to operate both with 2-D and 3-D interrogation regions. Note that the invention generates 3-D acoustic displays regardless of whether the visual display is 2-D or 3-D. The manner in which ultrasonic scanning signals are controlled, generated, and applied to a patient's body is well understood in the art and is therefore not described further.

If all one is interested in is velocity information in one direction, then it is sufficient to focus a single beam on a given sample volume and to sense and measure the Doppler shift of the return signals from the beam. In order to get information sufficient to identify flow velocity components within the sample volume in two dimensions (two non-parallel velocity components) then one must focus at least two beams on the sample volume from different angles (for example, by using interleaved element arrays). The transmission controller 104 will then need to generate two different groups of N signals to activate the N active elements in the transducer array and 2.N signals will then be returned to the array to make up the beam information for each sample volume. Analogously, in order to determine velocity components in all three directions in space, 3.N transmission signals must be applied to the array and N echoes will be returned to the array from the sample volume for beams focussed from three different angles, for a total of 3.N return signals that must be combined to form a total "3-D beam."

In general, therefore, if N elements are activated to contribute to each beam, then N.d echo signals will be generated and processed to extract flow velocity information with d independent velocity direction components. A similar analysis can be used to determine the required number of signals for non-linear or 2-D arrays, or when different numbers of elements in a linear array are activated to form beams. Such determinations are well understood in the field of ultrasonic imaging.

Ultrasonic echoes from the waves transmitted into the body return to the array in the probe 106. As is well understood, the piezoelectric elements in the array thereby convert the small mechanical vibrations caused by the echoes into corresponding electrical signals. The return signals sensed by the piezoelectric elements are applied to a bank of N.d amplifiers 116. The amplified return signals are then converted from analog to digital form in an A/D circuit 118, which will typically comprise a bank of N.d A/D converters, one for each return channel and beam angle.

After analog-to-digital conversion, the N.d channels of return signals are formed into m.d beams (d beams from each of the m sample volumes) using conventional beamforming circuitry 120. As is well known, beamforming groups the return signals in such a way that each portion of each signal corresponds to information from an identifiable portion of the interrogation region.

The return signals from the transducer 106 are typically modulated at high frequencies, containing both amplitude and phase information, and are thus properly viewed as complex numbers. As is conventional, the signals comprising each scan beam are therefore demodulated and decomposed into demodulated beam signals $Z1_1, \ldots, Z1_d, \ldots, Zm_1, \ldots, Zm_d$ (that is, one for each of the m.d beams generated to extract d velocity components from the m sample volumes) using known demodulation circuitry 122, and are then applied to the processing system 102.

Other conventional circuitry may be included in the system between the transducer array 108 (with subscripts dropped merely for the sake of simplicity) and the processing system 102 to carry out such known functions as time-gating, gain compensation, and diffraction compensation. This circuitry is not shown because it is well understood and would only needlessly complicate the figure.

The invention uses Doppler flow signals to generate its 3-D display. As is well known for this mode of operation, flow in each sample volume is determined based on the degree and direction of Doppler shift of the ultrasonic return signals. For scanning in planes, for example, with a linear array, the system detects the two in-plane components of the flow vector in each sample volume. Flow "left" and "right" is thereby conventionally defined as flow with a chosen velocity component to one side or other of a predefined reference line. With 2-D ultrasound arrays, flow vectors lying in different planes can be detected. Note that the labels "left" and "right" are arbitrary and could just as well be "up" and "down" or "in" and "out" or other non-parallel direction pairs. Merely for the sake of simplicity and clarity, it is assumed below that signals are sooner or later classified into the categories "left" and "right;" exceptions to this assumption are identified as such.

The processing system 102 according to the invention includes at least four sub-systems, each of which may be implemented either as part of a single, high-speed processor or connected group of processors, or as a dedicated processor or processor group. A Doppler processing subsystem 124 detects the envelope and decodes the Doppler shift information in the demodulated signals. An echo processing sub-system 126 determines the relative intensities of the portions of the N return signals after demodulation and Doppler envelope detection. Either or both of the Doppler and echo processing subsystems may include a dedicated processor for each of the N signal channels in order to increase processing speed.

The echo processing subsystem 126 cooperates with or includes a video processing subsystem 128 to generate an array of signal intensity values, which are stored in a memory 130 as a series of 2-D (or 3-D, depending on the application) image data frame arrays 132. Since the geometry of the scan beams is normally not in a form suitable for direct display, 2-D frame information (which may be planar sections of 3-D data) is applied to a conventional scan converter 134. The scan-converted data is then applied to a conventional video display system 136, which will include such known circuitry as a display driver and LCD or CRT screen. The generation of a visual display is well known and is therefore not described in further detail.

According to the invention, however, both the Doppler and echo-processed signal information is applied to an audio processing subsystem 138, which is described in detail below. As part of its processing, the audio processor needs information concerning the position of the transducer 106 in some predetermined coordinate system, such as the X-Y-Z system shown in FIG. 1. This coordinate system may, for example, be fixed relative to the display 136 or system console, in which case a known position sensor 140 is included to generate input signals to the processing system 102, and in particular to the audio processing subsystem, indicating the position of the transducer probe 106 in the predetermined coordinate system. As is explained below, the invention can do without the position sensor 140 as long as another reference point (such as the center element of the transducer array) is chosen as the origin of the coordinate system, and can be related to another coordinate system fixed relative to the user, the ultrasound console, or some other predetermined point.

The audio processing subsystem 138 generates 3-D audio signals that are applied, via a conventional amplifying speaker driver 142, to a left speaker 144 and a right speaker 146. The speakers may be free-standing, part of a "surround-sound" system, or even separate earplug speakers. It is preferred, however, that the speakers be the left and right speakers of a conventional stereo headphone, since a headphone is less affected by ambient noise and has the shortest path from the speakers to the user's auditory organs.

In FIG. 1, the user's head 148 is viewed from above. A reference direction vector is indicated by an arrow r. The reference direction vector preferably lies at the intersection of a horizontal plane that passes through the user's ears and a vertical plane midway between the user's ears. In the figures, three points in "hearing space" are indicated as h1, h2, and hm. The invention preferably generates a signal in hearing space for every sample volume. For 2-D scanning, for example, with a linear array, all points in hearing space preferably also lie in a plane in order to obtain the greatest correspondence between the position of a sample volume in the scan plane and the position of a point in hearing space. This is, however, not necessary. As is made clearer below, the invention allows substantially arbitrary mapping of points from sample volumes to hearing space. Moreover, sample volumes distributed in three dimensions (not all coplanar) may also be mapped to a 3-D hearing space.

To understand the concept of hearing space, imagine sitting in a center seat with one's eyes closed while listening to a symphony orchestra playing the 1812 *Overture* by Tchaikovsky. The violin section is to the conductor's left and near the front, the trombones and tubas to the right, and the percussion section (responsible for the cannon reports) at the rear of the stage and slightly to the right. During its most famous, rousing part, even with one's eyes closed, one would still be able to discern the relative positions in space of the different instrument groups, even though all sound is entering through either or both of only two channels: one's left and right ears. The brain therefore converts the sounds from the actual, physical positions of the instruments into corresponding mentally created positional signals within the user's head, that is, in hearing space. In this case, the ears receive signals from the equivalent of a "scan plane," since all the sounds are originating from roughly the same plane (the stage). One would, however, also be able to hear a burst of applause coming from above in the balcony, which would represent acoustic information coming from a 3-D interrogation region (the whole theater).

In reality, almost all human hearing is done in hearing space, which the brain automatically "maps" to physical space. In FIG. 1, the points h1, h2 . . . hm in hearing space correspond to the locations in physical space of the sample volumes sv1, sv2 . . . svm. The manner in which the mapping between sample volumes and points in hearing space is described below in detail. The main steps of the procedure are, however, as follows:

1) In a calibration step, determine the head-related transfer functions (HTRF) for a representative sonographer for predetermined calibration points in physical space.

2) Map the calibration points to corresponding sample volumes in a predetermined interrogation region.

3) Scan an actual interrogation volume and form beams corresponding to the actual sample volumes.

4) Using Doppler analysis techniques, decompose the beam information from the sample volumes into first and second channels. For 2-D scanning, the channels will typically—but need not be—be left-right, as is done at present for convention stereo 2-D acoustic displays.

5) Determine which calibration point each sample volume best corresponds to.

6) Filtering each of the channels of signals using the HRTF for the calibration point that corresponds to the sample volume.

7) Applying the HRTF-filtered signals to left and right speakers worn by the sonographer.

Before delving into these steps, some theory is helpful.

The general concepts of hearing space and head-related transfer functions (HRTF) are described in "Three-dimensional virtual acoustic displays," by Elizabeth M. Wenzel, which article she expanded in "Localization in virtual acoustic displays," PRESENCE: Teleoperators and Virtual Environments, Vol. 1, No. 1, MIT Press, March 1992.

The traditional theory of human hearing that has motivated most of the modern research on sound localization is the "duplex theory" developed by Lord Rayleigh, which held that the brain determined the apparent source of sound differently for high-frequency sound than for low-frequency sound. For high-frequency sound, Rayleigh concluded that the dominant factor in localization was the difference in intensity ($\Delta I$) sensed by the left ear as opposed to the right—the louder a sound is in the left ear, for example, the more from the left one assumes the sound to come. For low-frequency sound, however, he concluded that the dominant factor was the difference in time-of-arrival ($\Delta T$) at the respective ears—one assumes that a sound that reaches the right ear first began closer to the right ear.

The duplex theory failed to take into account, however, the position-dependent filtering caused by the interaction of an incoming sound wave with the folds of the hearer's outer ear (pinnae). As such, the theory is severely limited in its ability to account for the ability of hearers to precisely locate sounds on the median plane (elevation cues) and front-back discretion where interaural cues are minimal or absent (the sound is about as strong and arrives at about the same time at both ears). Moreover, the theory could not satisfactorily explain why hearers can establish that sounds are coming from outside the head in the natural environment—listeners perceive simple stereo stimuli over headphones as being inside the head even though the differences in the interaural temporal and intensity differences are appropriate to an external source.

One explanation for the weakness of the duplex theory is that it fails to take into account that $\Delta I$ and $\Delta T$ are frequency-dependent for a given sound location. Recent research has demonstrated that the shape and size of the pinnae, together with the head and shoulder, have a complex, frequency-dependent effect of both attenuating and phase-shifting incoming sound signals.

Figure 2:
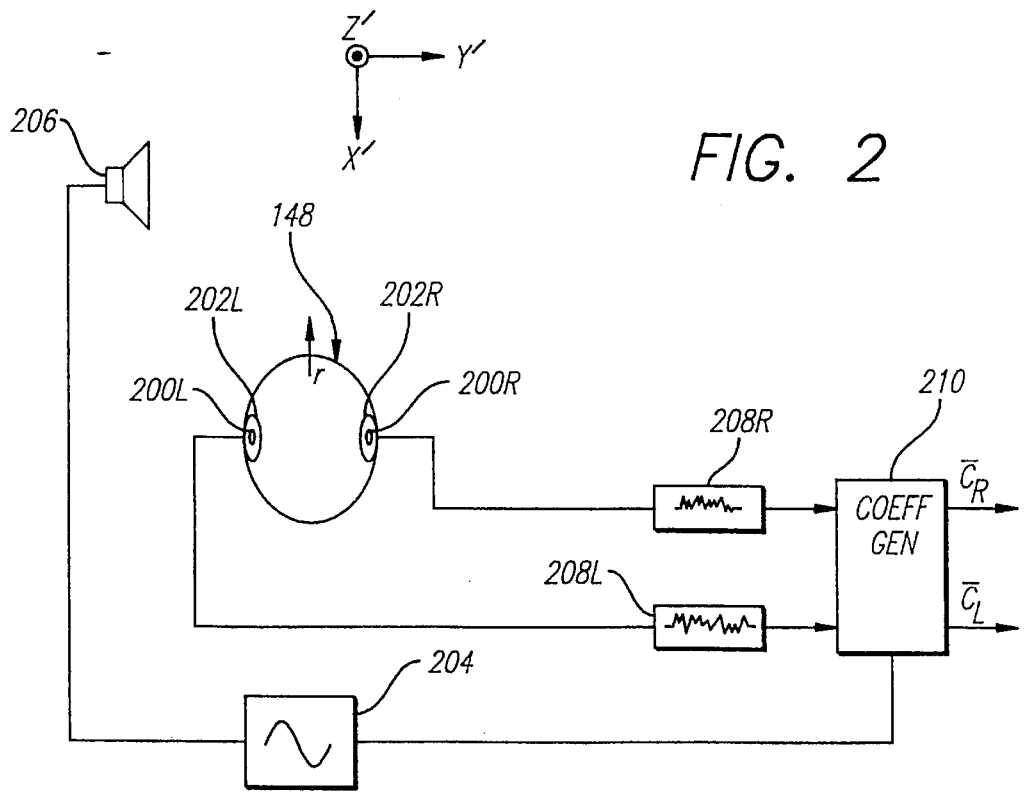
FIG. 2 illustrates the preferred method for calibrating filters according to the invention.
Figure 3:
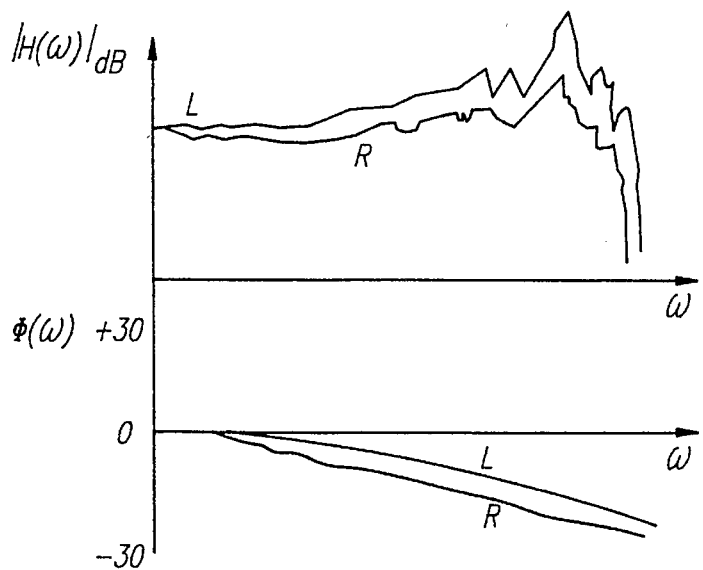
FIG. 3 is an illustrative plot of the frequency response of a human's ears to a sound impulse.
Figure 4:
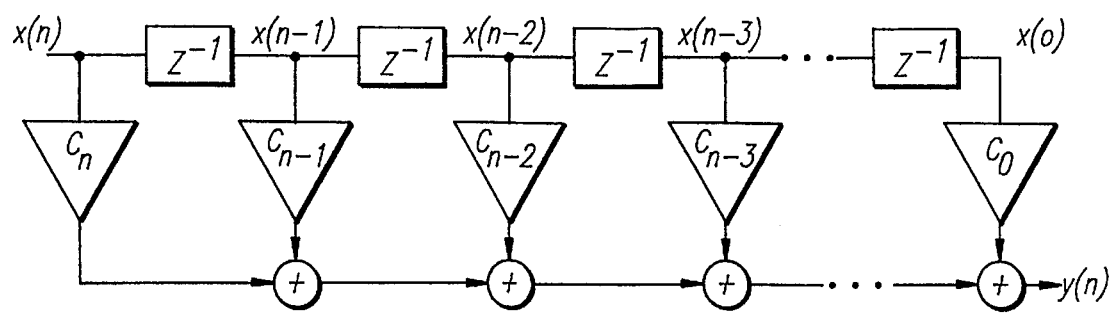
FIG. 4 is a block diagram of a finite impulse response (FIR) filter.

One way to incorporate the effect of pinnae to obtain precise localization cues is through the use of HRTF based on linear filtering techniques. This is a technique for creating digital filters based on measurements of finite impulse responses in the ear canals of either individual subjects or artificial heads. FIGS. 2–4 illustrates the preferred technique.

Microphones 200L and 200R are first placed in the left and right ear canals, that is, within the left and right pinnae 202L and 202R, respectively, and as close to the eardrums as is safely and comfortably possible, of either a "representative" human test person or of an artificial head with pinnae designed to resemble those of a representative human. A signal source 204 drives a loudspeaker 206 to create a sound signal resembling an impulse with a predetermined amplitude. The loudspeaker and microphones are precisely positioned in an x'-y'-z' coordinate system.

As is well known, such an impulse corresponds to a very short, sharp "click," which will contain a wide spectrum of frequencies of roughly equal amplitude. The outputs of the microphones are detected using conventional sensing and amplification circuitry 208L, 208R. As FIG. 2 illustrates in greatly simplified form, although the signal input to the loudspeaker is a short pulse of energy, the microphones will sense sound signals that have duration and varying amplitude, and they will almost never be the same in either respect, if for no other reason than that the ears are not perfectly identical.

FIG. 3 illustrates qualitatively a Bode plot of the amplitude and phase of the frequency-dependent characteristics of the signals that might be sensed by the left and right microphones 200L, 200R. $|H(\omega)|$ and $\phi(\omega)$ are the amplitude and phase shift of the ratio of the sensed sound signals to the input signal as a function of frequency $\omega$. As the Bode plot illustrates, above a certain high frequency, the sensed amplitude of the incoming sound signal drops. The pinnae attenuate certain frequencies more than others, and they do so differently. The pinnae (among other factors) thus serve to attenuate and phase-shift the input sound signal, in a frequency-dependent manner. In other words, they act as a filter.

Assuming one can determine $|H(\omega)|$ and $\phi(\omega)$, one would therefore know the way in which the input sound pulse gets changed from the loudspeaker to the microphone—one would know the head-related transfer function (HRTF) of the channel for the given loudspeaker location. (The channel is defined as the signal path from the input of the loudspeaker, where the input signal is pulse-like, to the output of the microphone, and will also be affected, for example, by the listener's shoulders and head.) The shape of $|H(\omega)|$ and $\phi(\omega)$ will almost always change whenever the position of the loudspeaker 206 changes relative to the position of listener's 148 head. Indeed, for each point in the x'-y'-z' physical space there will be a corresponding $|H(\omega)|$ and $\phi(\omega)$, and whenever a listener hears a sound with the amplitude and phase characteristics of a particular HRTF, she will tend to "hear" it as if it were coming from the corresponding point in the x'-y'-z' physical space.

According to the invention, the HRTF's for both ears of a representative listener are measured at many calibration points (typically, the loudspeaker will simply be moved) around the user in x'-y'-z' physical space, and parameters defining each HRTF are stored in the memory 130 (see FIG. 1) in a table 160 of HRTF coefficients. If 2-D scans are all that are to be done, then the calibration points should be chosen to lie in a plane, preferably in the horizontal x'-y' plane that includes the listener's eardrums. For Doppler flow scans with velocity components in three directions, the calibration points should be distributed both in the azimuth (left-right) and elevation (up-down) directions throughout the x'-y'-z' physical space, not all in one plane. The calibration is preferably done with the loudspeaker 206 and subject 148 in a sound-proofed, anechoic chamber so as to eliminate the effects of background noise and echoes on the determination of the transfer functions.

Digital implementations and operations on frequency-domain transfer functions are often slow, since the listener hears in the time domain and the time-domain signals would have to be converted in real time into the frequency domain using such known techniques as the Fast Fourier Transform (FFT). The signals would then later have to be reconverted into the time domain using inverse FFT techniques. Although there is plenty of time for such operations during the calibration step when the HRTF's are determined, the extra time required may not be available or desirable during actual scanning operations. According to the invention, the HRTF's are therefore implemented using time-domain, finite-impulse response (FIR) filters.

FIG. 4 illustrates the general structure of an FIR filter. As is well known, an FIR filter forms its output signal y(n) at time t=n as the weighted sum of the present and n previous values of the input signal x(n), where n represents integral multiples of the period at which the input signal is sampled. The structure of FIG. 4 implements the following sum:

$$y(n) = \sum_{i=0}^{n} c_{n-i} \cdot x(n-i) = \sum_{i=0}^{n} c_i \cdot z^{(i-n)} \cdot x(n)$$

so that:

$$\frac{y(n)}{x(n)} = \sum_{i=0}^{n} c_i \cdot z^{(i-n)}$$

where $z^{-m} = e^{-j\cdot\omega\cdot m}$ is the well-known "backward" time-shift function.

Note that the expression for y(n)/x(n) gives a frequency-dependent relationship between the output signal y(n) and the input signal x(n). By including enough previous values of x(n) and by choosing the coefficients (weights) $c_i$, properly, one can therefore duplicate or at least approximate a frequency-domain transfer function, even though the filtering is in the time domain. This can be done very fast, since it requires only that the n previous sampled values of the input signal should be stored in a shift register (implemented in hardware or as a memory array with suitable address generation) and multiplied by the appropriate set or vector $\bar{c} = c_i$ of filter coefficients. The design of FIR filters (including the manner of determining the number and values of filter coefficients) to produce a given frequency-domain response is well understood and is explained in such standard texts as *Digital Signal Processing* by Alan V. Oppenheim and Ronald W. Schafer, pp. 237–69, Prentice Hall, 1975. According to the invention, any such known method may be used to selects FIR coefficients to provide a filter with the amplitude and phase response of a measured HRTF.

It is also possible according to the invention to store the parameters of a frequency-domain filter and to operate in the frequency domain for signal processing, rather than store the coefficients of an FIR filter. Moreover, in order to reduce storage requirements and increase speed, it is also possible according to the invention to implement the HRTF's using infinite-impulse (IIR) filters, although care must then be taken to avoid the possibility of filter instability. The design of such IIR filters is also well known from standard texts such as Oppenheim and Schafer's.

A further consideration in determining the HRTF's at different calibration points is that not only the pinnae affect the input signal and contribute to the transfer function's characteristics—the loudspeaker and microphones do also. Furthermore, if one were to play back the filtered sounds through headphones for the subject to listen to, then the headphones themselves would attenuate and phase-shift the played-back signal.

Let $X1(\omega)$ be the frequency-domain signal from the source 204 that drives the loudspeaker at a given location relative to the listener in physical space. Let $Y1(\omega)$ be the resultant frequency-domain signal from the probe microphone at the eardrum. Let $X2(\omega)$ be the signal that drives the headphone and $Y2(\omega)$. The probe microphone's response to X1 can be written:

$$Y1 = X1.L.F.M$$

where $L=L(\omega)$ is the transfer function of the loudspeaker, $F=F(\omega)$ is the transfer function of the free field (the physical space between the loudspeaker and the pinnae) and $M=M(\omega)$ is the transfer function of the microphone.

The probe microphone's response to X2 can be written:

$$Y2 = X2.H.M$$

where H is the headphone-to-eardrum transfer function. Setting Y1=Y2 and solving for X2 gives:

$$X2 = X1.L.F/H$$

which shows that the desired filter transfer function $T=T(\omega)$ is given by $$T = L.F/H$$

Thus, if the signal X1 is filtered by T to produce X2, the signals Y1 and Y2 produced at the probe microphone would be the same. This also shows that one can "divide out" the effects of the loudspeaker, headphone, and microphone that are used in the system as long as one can determine $L(\omega)$, $H(\omega)$, and $F(\omega)$. These transfer functions may be easily determined using known measurement techniques—indeed, they are often specified in data sheets provided by the manufacturers of such devices.

According to the invention, a pair of transfer functions T for the left and right ears of a listener are measured in the time domain for each calibration point. A table of FIR HRTF "location filter" coefficients 160 is built up in the memory 130 (FIG. 1) by first transforming the measured and sampled time-domain signals into the frequency domain, preferably by using known techniques such as the FFT. The spectral effects of the original calibration loudspeakers and the headphones (that is, of $L(\omega)$ and $H(\omega)$) are then divided out according to the relation above, and then the FIR coefficients are determined (using known methods) that approximate the remaining function, which also represents a transformation back into the time domain. It is also possible to eliminate the effects of loudspeaker and headphone transfer functions by operating wholly in the time domain, but in such case conversion using the FFT and division must be replaced by the known operation of deconvolution.

These calculations are carried out in a coefficient generator 210 (FIG. 2), which will typically be a conventional, properly programmed processor with data sampling circuitry. As its name implies, the coefficient generator 210 calculates the set of FIR coefficients $\bar{c}_L$ and $\bar{c}_R$ for the measured transfer functions of the left and right ears for each calibration point.

Assuming enough calibration points are chosen, measured, and represented using FIR coefficients, then HRTF parameters for points between calibration points may be calculated from nearest neighboring points by standard interpolation. Alternatively, as long as the resolution of calibration points is high enough, one may simply assign as the HRTF for intermediate points the HRTF of the closet calibration point. The principle of the invention is that if, using headphones, one produces ear canal wave forms identical or close to those produced by a free-field source, then one can duplicate the free-field experience.

Reference is made above to a "representative" listener who is used in the calibration step. Since it will often be impractical (although possible according to the invention) to measure each potential user's HTRF's or to conduct extensive training, one should keep in mind that there may be significant differences in localization behavior of different individuals. Recent psychophysical studies have indicated, however, that it is possible to create HRTF's that are general enough that they can be used for a wide range of listeners. The ability of experienced listeners to localize sounds has been shown to be degraded so little by such "standard" HRTF's that they should still be able to "hear" position in hearing space that closely corresponds to the calibration point in physical space. This has proven true even for elevation cues, which are less robust. (It's harder to judge the relative height of two sound sources than it is to judge their relative left-right position, which is in the azimuth plane.) Standard HRTF's should be compiled using one or more listeners whose sense of hearing is good. The resulting transfer function sets can then either be averaged, reduced (for example, by finding an optimal least-squares approximation) or otherwise empirically adjusted. In general, most listeners should be able to obtain useful directional information from the auditory display according to the invention without needing individually calibrated HRTF's.

Figure 5:
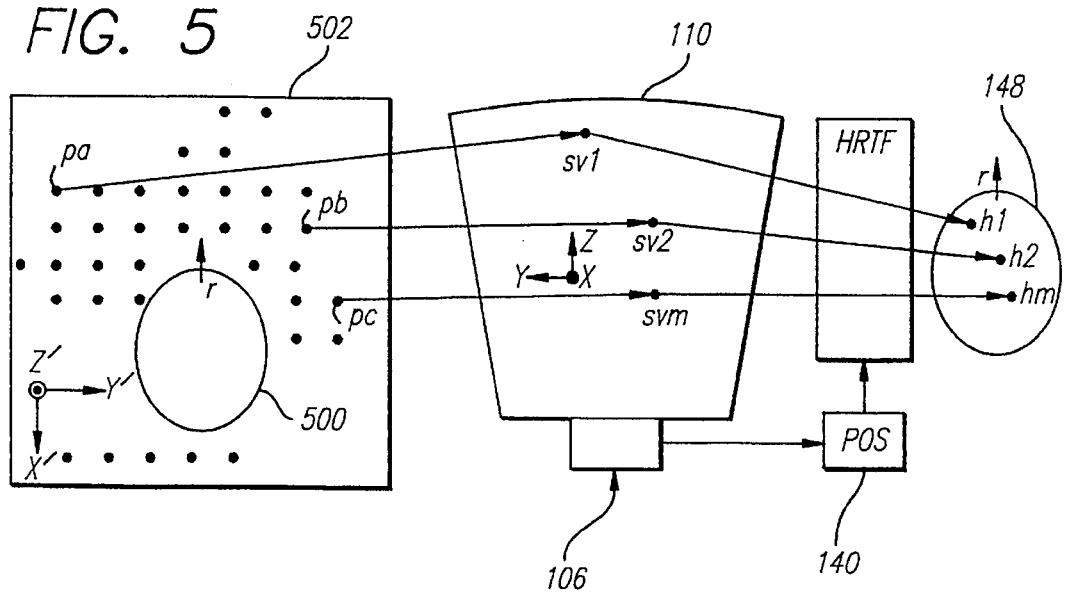
FIG. 5 illustrates various coordinate systems and mappings used in the invention.

FIG. 5 illustrates the general principle used in the operation of the invention. Transfer function coefficients are determined for the representative listener 500 in the (preferably anechoic) test area 502 for a series of calibration points p distributed around the listener's 500 head. For any given scan and transducer, the shape of the scan space (the interrogation region) will be known. As part of the calibration process, the points in x'-y'-z' calibration space are mapped onto predetermined reference scan points in the x-y-z scan space, which is equivalent to assigning, for each predetermined reference scan point, a pair of HRTF coefficient sets. The combined information from the position sensor 140 and the beamforming process locates the current actual scanned sample volume in the x-y-z system and thus enables selection of the corresponding HRTF coefficients based on the precalculated mapping function from calibration to scan space. By applying the HRTF's, the Doppler velocity signals in scan space are mapped onto points such as h1, h2, hm in hearing space.

Note that although all points in the scan space will of necessity be on the same side of the transducer array 106, the mapping is arbitrary. For example, by placing the origin of the x-y-z coordinate system in the "middle" of the interrogation region, the sample volume svm can be mapped onto a hearing space position "behind" the listener 148. The reference origin for the hearing as well as calibration space is preferably the mid-point of the line that connects the left and right ears of the respective listeners. The reference origin for the scan space may be chosen in either of two ways. One is to use the center point of the transducer array surface or any point fixed relative to it and the other is to choose a point that is fixed relative to the console of the imaging system. In the former case, the position sensor 140 will be implemented in software, with the processing system generating position signals based on the known or fixed geometry of the transducer and beam focussing. In the latter case, the 3-D position sensor 140 should be included and should include hardware for tracking the moving position of the array. Once the reference origins in both spaces are determined and the relative size scaling parameters are specified (in any known way), the coordinates of position vectors in both spaces may be related by simple geometric transformations.

Figure 6:
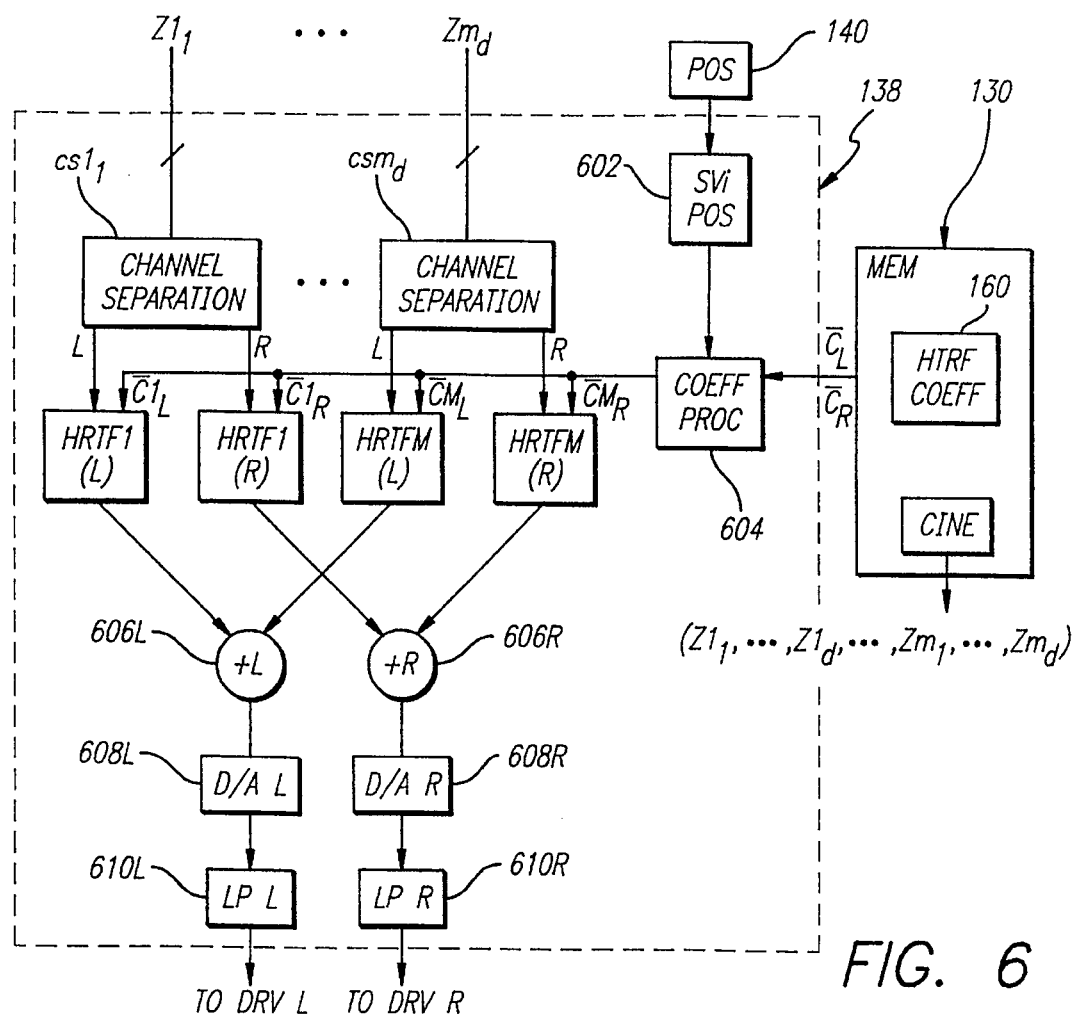
FIG. 6 is a block diagram of an audio processor used in the invention.

FIG. 6 is a block diagram that illustrates the main components of the audio processor 138. Each of the demodulated beam signals $Z1_1, \ldots, Z1_d, \ldots, Zm_1, \ldots, Zm_d$ is applied to a respective channel separation and projection circuit $cs1_1, \ldots, cs1_d, \ldots, csm_1, \ldots, csm_d$ (only two of which are shown in FIG. 6 for the sake of simplicity). Recall that each demodulated beam signal corresponds to one of the d beams focussed into each of the sample volumes sv1, ..., svm.

The system according to the invention generates audio signals that are applied to drive the left and right speakers 144, 146 (FIG. 1), which generate sound for the left and right ears of the user. Consequently, the velocity information contained in the demodulated beam signals $Z1_1, \ldots,$ $Z1_d, \ldots, Zm_1, \ldots, Zm_d$ are eventually combined and converted into left-right components (assuming the speakers 144, 146 have only one coil each), regardless of in which coordinate system they are defined and generated. The d-dimensional information in the beam signals must therefore sooner or later be projected down to two single-variable functions of time, that is, to one-dimensional drive signals for the speakers.

As is mentioned above, the demodulated beam signals may be separated into two components and their corresponding components may be combined in any conventional way, such as left/right, up/down, positive/negative, forward/reverse, in/out, and so on, as long as one decides in advance how these directional definitions relate to predominantly left/right signals that the user will hear and interpret. These concepts are known in the art, as is the design of channel separation and projection circuits such as $cs1_1, \ldots,$ $cs1_d, \ldots, csm_1, \ldots, csm_d$, which perform the required signal separation and projection in any known manner. If a 2-D array is used to determine flow velocity with components in three independent directions (d=3), then the channel separation and projection circuits will incorporate any known procedures for projecting and incorporating out-of-plane velocity components into the separated output signals.

As an example, for conventional 2-D scans, each demodulated beam signal will have separate (and separated) in-phase (I) and quadrature (Q) components. The channel separation and projection circuits $cs1_1, \ldots, cs1_d, \ldots,$ $csm_1, \ldots, csm_d$ will in such case include known delay and Hilbert-transformation circuits, whose outputs are combined to create forward and reverse signals, which in turn correspond to detected Doppler flow velocity components in forward and reverse directions relative to a predetermined zero-velocity reference. The channel separation and projection circuits will then have as their output signals left- and right-channel signals that contain the I/Q information but in a form corresponding to left/right Doppler-detected flow. The output signals from the channel separation and projection circuits $cs1_1, \ldots, cs1_d, \ldots, csm_1, \ldots, csm_d$ are thus labeled "L" (left) and "R" (right) in FIG. 6 by way of example only.

As an analogy to the orchestra, each beam signal corresponds to the sound coming from a particular instrument (or section) that is located at a known place on the stage. The difference is that whereas each musician (at least in most symphony orchestras) generates sound while sitting in the same place, the beam signals represent the position a vector field, where the velocity of flow is detected acoustically at each point.

Using information from either the position sensor 140 or from positional data relative to the transducer derived in the conventional manner from the beamformer, a sample volume position circuit 602 determines the position in scan space (x-y-z) of the sample volumes that each of the beam signals $Z1_1, \ldots, Zm_d$ comes from. This circuit may comprise a simple look-up table containing the geometry of the interrogation region, or it may include (or be part of) a processor that calculates sample volume position based on the position signals and beamforming data. It is known how one determines sample volume position.

A coefficient processor 604 (which may be a processor shared by other parts of the system on a time-shared basis) receives the sample volume position data for each sample volume and calculates which calibration point each sample volume maps back to. The coefficient processor then addresses the HRTF coefficient portion of the memory 130 to fetch the left and right FIR coefficient sets $\bar{c}_L$ and $\bar{c}_R$ for that calibration point. Alternatively, if the sample volume maps to a point in the physical calibration space that lies between calibration points, then the coefficient processor may select (for example, by examining a pre-stored table)

either the coefficient set for the closest calibration point, or it may employ conventional interpolation methods to obtain HRTF coefficient sets for the intermediate point.

For each channel $Z1_1, \ldots, Zm_d$, there is a left and a right HRTF circuit, which is preferably an FIR circuit as shown in FIG. 4. In FIG. 6, HRTF1(L) and HRTF1(R) are, for example, HRTF filters for the left and right ear, respectively that will filter the channel-separated signals of the beam signal $Z1_1$.

Once the coefficient processor 604 has determined which calibration point to map each sample volume from, and has downloaded from the memory 130 the corresponding coefficient sets for each channel $Z1_1, \ldots, Zm_d$, it loads the left and right FIR coefficient sets into the left and right HRTF filters for the corresponding channels. For example, coefficient sets $\overline{cm}_L$ and $\overline{cm}_R$ are loaded into the HRTF filters HRTFm(L) and HRTFm(R), respectively.

The HRTF filters then filter the input channel data. The filtered outputs of the left-ear HRTF filters are then combined (and scaled, as needed) in an adding circuit 606L, whose output is converted from digital to analog form in a D/A converter 608L, low-pass filtered as needed to reduce high-frequency noise in a conventional LP filter 610L, and then passed as the left drive signal to the loudspeaker driver 142 (FIG. 1). The filtered outputs of the right-ear HRTF filters are similarly processed by the adder 606R, D/A converter 608R, LP filter 610R and are passed as the right drive signal to the loudspeaker 142.

As an optional feature, the system may include a cine memory, which stores the data from earlier scans. This data either is or can be used in a known way to reconstruct the beam signals $Z1_1, \ldots Zm_d$. Rather than operating on beam data in real time, the invention may thus be used to generate 3-D acoustic displays of previously recorded examinations.

To use the invention, the sonographer conducts a normal ultrasound flow scan, but wears the headphones. Rather than hearing simple left-right sound, she will hear an acoustic representation of flow that comes from "all around" and she will therefore more easily be able to detect changes in the flow. Compared with the known stereo acoustic presentation based on Doppler information from a single sample volume, the invention generates an acoustic display with much richer relational information, since it derives its signals from interactions of multiple Doppler sample volumes in different spatial locations.

We claim:

1. An ultrasonic imaging system with a three-dimensional acoustic display mapping an image interrogation volume onto an audible, three-dimensional acoustic space of an operator.

2. An ultrasonic imaging system, comprising:

transducer means for scanning an interrogation region of a patient's body at a plurality of scanned sample volumes;

a beamformer forming a beam of returned signals from each respective scanned sample volume for each of a predetermined number of independent velocity directions;

a three-dimensional acoustic display system that includes:

channel separation means for converting each beam into a plurality of channel signals;

filter selection means for selecting, for each channel signal, one of a plurality of predetermined head-related transfer function (HRTF) parameter sets according to a predetermined function of the position in the interrogation region of the corresponding scanned sample volume and of the respective independent velocity direction, each HRTF corresponding to left-ear and right-ear response functions to a calibration sound generated at a calibration point in a calibration space, which calibration point corresponds to a predetermined position in the interrogation region;

HRTF filter means for filtering each channel signal as a predetermined function of the corresponding HRTF parameter set;

signal combination means for combining the HRTF filtered channel signals into left and right audio output signals; and speaker means including first and second speakers for applying the left and right audio output signals to the left and right ears of a user and for generating combined audio display signals, the user thereby hearing the combined audio display signals with non-colinear apparent points of origin.

3. A system as defined in claim 2, further including a cine memory for pre-storing scan data, in which the HRTF filter means receives as the channel signals those pre-stored in the cine memory.

4. A method for generating an acoustic display of an ultrasound scan comprising the step of generating the display three-dimensionally by mapping an image interrogation volume onto an audible, three-dimensional acoustic space of an operator.

5. A method for generating an acoustic display of an ultrasound scan comprising the step of generating the display three-dimensionally, which in turn comprises the following sub-steps:

A) in a calibration mode:

1) determining a pair of head-related transfer functions (HRTF) for each of a plurality of calibration points in a predetermined calibration space, the HRTF's in each pair corresponding to left-ear and right-ear response functions to a calibration sound generated at the respective calibration points; and 2) mapping the position of the calibration points in the calibration space to respective reference sample volumes located in a predetermined ultrasonic interrogation region;

B) in an operational mode:

1) scanning the interrogation region at a plurality of scanned sample volumes and forming a beam of returned signals from each respective scanned sample volume for each of a predetermined number of independent velocity directions;

2) separating each beam into a plurality of channel signals;

3) selecting for each channel signal one of the HRTF's as a predetermined function of the position in the interrogation region of the corresponding scanned sample volume;

4) filtering each channel signal using the HRTF for the calibration point that corresponds to the sample volume;

5) combining the filtered channel signals into left and right audio output signals; and 6) applying the left and right audio output signals to first and second speakers that are oriented substantially toward the left and right ears of a user and that generate combined audio display signals, the user thereby hearing the combined audio display signals with non-colinear apparent points of origin.

* * * * *